United States Patent [19]
Grundke et al.

[11] Patent Number: 5,897,540
[45] Date of Patent: Apr. 27, 1999

[54] DEVICE FOR THE DRAINAGE OF UNCONTROLLED URINE RELEASE

[75] Inventors: Reinhold Grundke, Burghausen; Wilhelm Jaeniche, Kehl; Harald Lehmann, Langenau, all of Germany

[73] Assignee: Tarob Consultants, Ltd., Channel Islands

[21] Appl. No.: 08/911,910

[22] Filed: Aug. 15, 1997

[30] Foreign Application Priority Data

Aug. 21, 1996 [DE] Germany .................. 196 33 605

[51] Int. Cl.$^6$ .................................................. A61F 5/44
[52] U.S. Cl. ................................. 604/352; 604/349
[58] Field of Search ............................. 604/349–353, 604/345, 331

[56] References Cited

U.S. PATENT DOCUMENTS

| 2,789,560 | 4/1957 | Weimer | 604/349 |
| 3,161,197 | 12/1964 | Glas et al. | |
| 3,339,551 | 9/1967 | Stoutenburgh | 604/349 |
| 3,631,857 | 1/1972 | Maddison | 604/349 |
| 3,863,638 | 2/1975 | Rogers et al. | 604/352 |
| 4,656,675 | 4/1987 | Fajnsztajn | 604/349 |
| 4,685,913 | 8/1987 | Austin . | |
| 4,710,169 | 12/1987 | Christopher | 604/349 |
| 4,731,064 | 3/1988 | Heyden . | |
| 4,846,816 | 7/1989 | Manfredi | 604/323 |
| 4,865,595 | 9/1989 | Heyden | 604/352 |
| 5,284,159 | 2/1994 | Wilk | 604/349 |
| 5,380,312 | 1/1995 | Goulter . | |
| 5,423,784 | 6/1995 | Metz | 604/349 |
| 5,662,631 | 9/1997 | Marx | 604/349 |

FOREIGN PATENT DOCUMENTS 669063  3/1952  United Kingdom .

Primary Examiner—Mark O. Polutta
Attorney, Agent, or Firm—Rothwell, Figg, Ernst & Kurz, p.c.

[57] ABSTRACT

A device to drain uncontrolled urine release in male persons has a body (10) made of soft, pliable material whose central cross section forms an approximately circular cylindrical mantel (12) matched to the penis cross section, to which a collecting chamber (13) connects on one end which is funnel-shaped, narrowing in the direction of a hose connection (14). On the other open end, the mantel (12) is subdivided into multiple tongues (16a, 16b, 16c) through interruptions (18a, 18b, 18c) which follow each other in a circumferential direction, and on the body (10) at the transition from the closed mantel (12) to the tongues (16a, 16b, 16c), a soft elastic pliable sleeve (35) is applied or can be applied, which is suitable for enclosing the tongues elastically from outside.

8 Claims, 1 Drawing Sheet

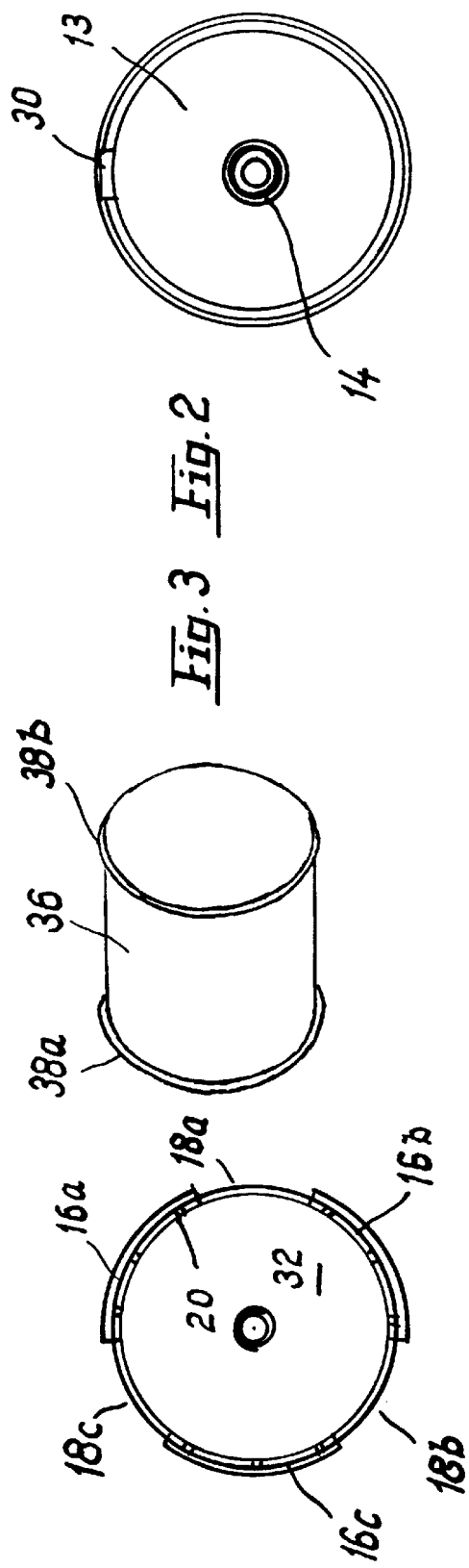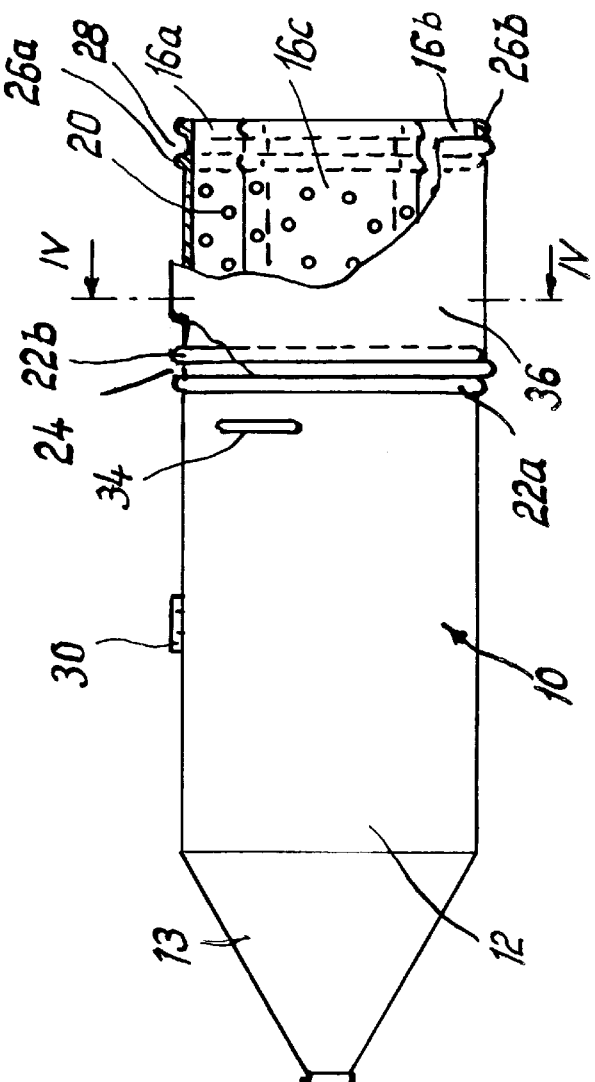

DEVICE FOR THE DRAINAGE OF UNCONTROLLED URINE RELEASE

BACKGROUND OF THE INVENTION

The invention concerns a device for the drainage of uncontrolled urine release in males.

FIELD OF THE INVENTION

In the case of uncontrolled urination (incontinence), according to the current state of the school of medicine, either a catheter is inserted into the bladder which drains the urine into a collection receptacle, or drainage is dispensed with and the person suffering from incontinence is diapered. Both procedures have disadvantages, for example, the insertion of a catheter requires skill and is connected with the danger of infection, while in the case of diapers, the soiling of laundry cannot be excluded. Furthermore, both processes are relatively expensive since, on an average about seven diapers per day are needed, or the catheter must be changed after five, at most seven, days and this implies high costs.

SUMMARY OF THE INVENTION

The purpose of the invention is to create a device which is easy to manage and use, which, when properly used, prevents the soiling of laundry, which interferes as little as possible with freedom of movement of the patient, and which is also re-usable multiple times.

The solution to this problem is provided by a device for the drainage of uncontrolled urine release in male persons, which has a basic body made of pliable material with a cross section in the form of an approximately circular cylindrical mantel adjusted to the cross section of the penis, to which a funnel-shaped collecting chamber is connected on one end, in the direction of a hose connection, while the other open end is connected to a soft elastic conforming holding sleeve.

Before the device is applied, the sleeve is rolled up onto the mantle, whereupon the device is placed on the penis and then the sleeve is unrolled in order to hold the device firmly through skin contact, at least with the tongues, which, since they are made of soft elastic pliable material, cannot interfere with blood flow in the penis even if it swells. Subsequently, the hose connection is established between the hose connection and a collecting bag. The funnel-shape of the collecting chamber prevents back-flow during urination. The tongues assure that, after the application of the device on the penis, the area necessary for unrolling the sleeve is available.

The device can be worn not only while lying, but also while standing, walking and sitting.

An especially suitable design consists, on the one hand, in the basic body at the transition from the closed mantel to the tongues and, on the other hand, at the end of the tongues, a pair of toruses which are placed running in a circumferential direction and forming a furrow between them open toward the outside, and an elastic pliable sleeve provided on its open end with a torus to engage in one of these furrows. This design makes it possible to change the sleeve easily.

Preferably, the basic body consists of soft plastic and the sleeve of latex.

A suitable form is for the hose connection to connect in an axial direction to the funnel-shaped collecting chamber.

It is preferable to provide a connecting point on the mantel for a rinsing device where, according to an advantageous design, the connecting point is formed as a separated membrane which is suitable for the connection of the cone of a single-use spray.

According to a further suitable design, the mantel has a ventilation opening near the transition to the tongues.

In another advantageous design, the tongues are provided with stamped slots to improve adhesion to the skin.

This is explained in greater detail using the following description of a sample embodiment of the invention represented in the drawing.

BRIEF DESCRIPTION OF THE DRAWINGS

The following are shown:

FIG. 1 a side elevation view, with portions broken away, of the device, in accordance with the invention, FIG. 2 an end view of the device shown in FIG. 1 from the left, FIG. 3 a perspective representation of the sleeve and, FIG. 4 a cross section through the basic body, according to the line IV—IV in FIG. 1.

DETAILED DESCRIPTION OF THE INVENTION

The device shown has a basic body 10 made of soft plastic, which consists of a circular cylindrical mantel 12 and a collecting chamber 13 which tapers conically attached to one end of it, with a hose connecting tube 14 attached to one end of it. From the end of the basic body 10 facing away from the collecting chamber 13, tongues 16a, 16b and 16c run at equal distances in the circumferential direction, which are separated from each other by three interruptions 18a, 18b and 18c following each other sequentially in the circumferential direction, where the central angle of the tongues is somewhat larger than that of the interruptions. The tongues 16a through 16c are provided with stamped slots 20 which serve to improve skin adhesion and prevent sliding of the device.

The end of the mantel 12 facing the tongues 16a through 16c is provided with a pair of circumferential toruses 22a and 22b which enclose, between themselves, a furrow 24 which places outward.

A similar pair of toruses 26a and 26b is provided on the free ends of the tongues 16a through 16c, and includes a furrow 28 running in a circumferential direction, which is divided into three sections by the interrupts 18a through 18c.

The mantel 12 contains a divided membrane 30 which is suitable for making it possible to apply the cone of a one-use spray in order to rinse the internal space 32 surrounded by the mantel 12.

A slit-shaped opening 34 is provided for ventilation of the internal space.

A sleeve 36 made of latex is provided on its two open ends with toruses 38a and 38b in the circumferential direction, dimensioned in such a manner that the sleeve 36 can enclose the tongues 16a through 16c in a closely lying position approximately continuing the mantel 12, and at the same time the toruses 34a and 34b can extend into the furrows 24 and 28.

Before use, the sleeve 36 is rolled back in the direction of the mantel 12, with its end which is provided with a torus 38b, where the torus 38a remains in the furrow 24. Then the device is placed on the penis and positioned, whereupon the sleeve 36 is unrolled until the torus 38b extends into the furrow 28. As a result, the tongues 15a through 16c are laid against the penis in order to hold the device, where however the tongues can bend if the penis swells.

We claim:

1. A device for draining uncontrolled urine release in male persons, the device having a body comprising soft, pliable material having an average cross section forming an approximately circular cylindrical mantel corresponding to a penis cross section, the body having a first end with a funnel-shaped collecting chamber which narrows in a direction of a hose connection, the body having an opposite open end, said mantel being subdivided through interruptions into several tongues, said body having a transition from said mantel to said tongues where a soft elastic pliable sleeve is attachable, which sleeve is suitable for surrounding the tongues elastically from outside, wherein, on said body at said transition from said mantel to said tongues, as well as at an opposite end of said tongues, a pair of toruses is located, adjacent said tongues and running in a circumferential direction so as to form an outwardly open furrow adjacent opposite ends of said tongues, and wherein said sleeve has connected thereto at opposite open ends thereof a torus, which fits within and is engageable with a corresponding furrow located adjacent said tongues.

2. The device of claim 1 for draining uncontrolled urine release, wherein the body comprises soft plastic.

3. The device of claim 2 for draining uncontrolled urine release, wherein the sleeve is made of latex.

4. The device of claim 3 for draining uncontrolled urine release, wherein the hose connection connects in the axial direction to the funnel-shaped collecting chamber.

5. The device of claim 4 for draining uncontrolled urine release, wherein on the mantel there is provided a connecting point for a rinsing device.

6. The device of claim 5 for draining uncontrolled urine release, wherein the connecting point has the form of a separated membrane which is formed for the connection of the cone of a single-use spray.

7. The device of claim 6 for draining uncontrolled urine release, wherein the mantel has a ventilation opening near the transition to the tongues.

8. The device of claim 7 for draining uncontrolled urine release, wherein the tongues are provided with stamped slots to improve skin adhesion.

* * * * *